United States Patent
Pyro et al.

(10) Patent No.: US 12,161,407 B2
(45) Date of Patent: Dec. 10, 2024

(54) MULTIPLE-MODALITY ABLATION PROBE TECHNIQUES

(71) Applicant: GYRUS ACMI, INC., Southborough, MA (US)

(72) Inventors: Jan T. Pyro, Shrewsbury, MA (US); Charles Baker, Rogers, MN (US)

(73) Assignee: Gyrus ACMI, Inc., Westborough, MA (US)

( * ) Notice: Subject to any disclaimer, the term of this patent is extended or adjusted under 35 U.S.C. 154(b) by 914 days.

(21) Appl. No.: 17/184,701

(22) Filed: Feb. 25, 2021

(65) Prior Publication Data

US 2021/0275248 A1 Sep. 9, 2021

Related U.S. Application Data

(60) Provisional application No. 62/984,654, filed on Mar. 3, 2020.

(51) Int. Cl.
*A61B 18/26* (2006.01)
*A61B 17/00* (2006.01)
(Continued)

(52) U.S. Cl.
CPC ...... *A61B 18/26* (2013.01); *A61B 2017/0034* (2013.01); *A61B 2017/00738* (2013.01);
(Continued)

(58) Field of Classification Search
CPC ........... A61B 2018/00172; A61B 2018/00982; A61B 2018/00994; A61B 2018/202;
(Continued)

(56) References Cited

U.S. PATENT DOCUMENTS 5,368,558 A 11/1994 Nita
2002/0002366 A1* 1/2002 Grasso, III ............. A61B 18/26
606/2.5
(Continued)

FOREIGN PATENT DOCUMENTS

CN 202654235 U 1/2013
CN 203724216 U 7/2014
(Continued)

OTHER PUBLICATIONS

English (Machine) Translation of CN-202654235U, Jan. 9, 2013, Liu, Jianjun et al., 4 pages (translation retrieved from Google Patents) (Year: 2013).*
(Continued)

*Primary Examiner* — Ronald Hupczey, Jr.
*Assistant Examiner* — Bradford C. Blaise
(74) *Attorney, Agent, or Firm* — Schwegman Lundberg & Woessner, P.A.

(57) ABSTRACT

A multiple-modality ablation probe can include a tube configured to transmit mechanical modality energy from a first end to an obstruction in contact with a second end. A first optical transmission media can extend along the tube to transmit laser modality energy from a laser energy source to the obstruction. A connector assembly can be mechanically coupled with the first end of the tube and with the first end of the first optical transmission media. The connector assembly can be configured for user-attachment and detachment of
(Continued)

the tube and the first optical transmission media with a mechanical energy source coupling and a laser energy source coupling, respectively.

21 Claims, 8 Drawing Sheets

(51) Int. Cl.
*A61B 17/32* (2006.01)
*A61B 18/00* (2006.01)
*A61B 18/22* (2006.01)

(52) U.S. Cl.
CPC .............. *A61B 2017/320069* (2017.08); *A61B 2018/00172* (2013.01); *A61B 2018/00982* (2013.01); *A61B 2018/00994* (2013.01); *A61B 2018/225* (2013.01)

(58) Field of Classification Search
CPC ...... A61B 2018/2035; A61B 2018/225; A61B 18/20; A61B 18/201; A61B 18/26; A61B 2017/0034; A61B 2017/00738; A61B 2017/320069
See application file for complete search history.

(56) References Cited

U.S. PATENT DOCUMENTS

| | | | | |
|---|---|---|---|---|
| 2012/0253333 | A1* | 10/2012 | Garden | ................ A61B 18/203 606/9 |
| 2014/0276101 | A1* | 9/2014 | Asselin | ................ A61B 5/0084 600/407 |
| 2017/0119470 | A1* | 5/2017 | Diamant | ............ A61B 18/1492 |

FOREIGN PATENT DOCUMENTS

| | | |
|---|---|---|
| CN | 203943716 U | 11/2014 |
| CN | 104473674 B | 3/2017 |
| CN | 107773304 A | 3/2018 |
| WO | WO-2021178186 A1 | 9/2021 |

OTHER PUBLICATIONS

"International Application Serial No. PCT/US2021/019523, International Search Report mailed May 20, 2021", 5 pgs.
"International Application Serial No. PCT/US2021/019523, Written Opinion mailed May 20, 2021", 7 pgs.
"International Application Serial No. PCT/US2021/019523, International Preliminary Report on Patentability mailed Sep. 15, 2022", 9 pgs.

* cited by examiner

MULTIPLE-MODALITY ABLATION PROBE TECHNIQUES

PRIORITY AND RELATED APPLICATIONS

This application claims the benefit of priority to Pyro et al., U.S. Provisional Patent Application Ser. No. 62/984,654, titled, "MULTIPLE-MODALITY ABLATION PROBE TECHNIQUES", filed on Mar. 3, 2020, and which is hereby incorporated by reference herein in its entirety.

FIELD OF THE DISCLOSURE

The present document relates to techniques for breaking obstructions such as physiologic calculi or "stones" using lithotripsy, more particularly to techniques for breaking the obstructions using more than one modality.

BACKGROUND OF THE DISCLOSURE

Medical endoscopes were first developed in the early 1800s and have been used to inspect inside the body. A typical endoscope consists of a distal end comprising an optical or electronic imaging system and a proximal end with controls for manipulating the tools and devices for viewing the image, with a solid or tubular elongate shaft connecting the ends. Some endoscopes allow a physician to pass tools or treatments down a hollow channel, for example, to resect tissue or retrieve objects.

Over the past several decades, several advances have been made in the field of endoscopy, and in particular relating to the breaking up of physiologic calculi in the bile ducts, urinary tract, kidneys, and gall bladder. Physiological calculi in these regions may block ducts and cause a patient a substantial amount of pain and therefore must be broken down and/or removed. Different techniques have been developed to break up stones, including ultrasonic lithotripsy, pneumatic lithotripsy, electro-hydraulic lithotripsy (EHL), and dissolution of calculi using green light, YAG, or holmium lasers.

SUMMARY OF THE DISCLOSURE

A multiple-modality ablation probe can include a tube configured to transmit mechanical modality energy from a first end to an obstruction in contact with a second end. A first optical media can extend along the tube to transmit laser modality energy from a laser energy source to the obstruction. A connector assembly can be mechanically coupled with the first end of the tube and with the first end of the first optical media. The connector assembly can be configured for user-attachment and detachment of the tube and the first optical media with a mechanical energy source coupling and a laser energy source coupling, respectively.

This section is intended to provide an overview of subject matter of the present patent application. It is not intended to provide an exclusive or exhaustive explanation of the invention. The detailed description is included to provide further information about the present patent application.

DETAILED DESCRIPTION

A number of rigid, solid or tubular shaft-based lithotripsy devices that use ultrasonic or pneumatic mechanical energy to break the stone into smaller pieces for easier removal from the patient's urologic system have been developed. Ultrasonic or acoustic frequency energy is transmitted down a stiff metal shaft and delivered by contact to a kidney stone. Laser lithotripsy uses an optical transmission media or optical pathway such as one or more optical fibers to transmit laser energy from a laser source to the target obstruction.

Choice of which lithotripsy modality to use, time-varying mechanical ablation energy or laser ablation energy, can be guided by the type, size, composition, or combinations thereof, of the obstruction to be broken. Some procedures can be carried out more efficiently using more than one modality as the obstructions can very internally as well as from one obstruction to the next within a single procedure. Certain techniques require that an instrument of one modality of breaking the obstruction be removed from the endoscope to accommodate insertion of an instrument of another modality. Such "instrument swapping" techniques may incur inefficiencies and hurdles associated with exchanging the single-modality probes within the lumen and shutting down and initiating the associated equipment of the different modalities.

Figure 1:
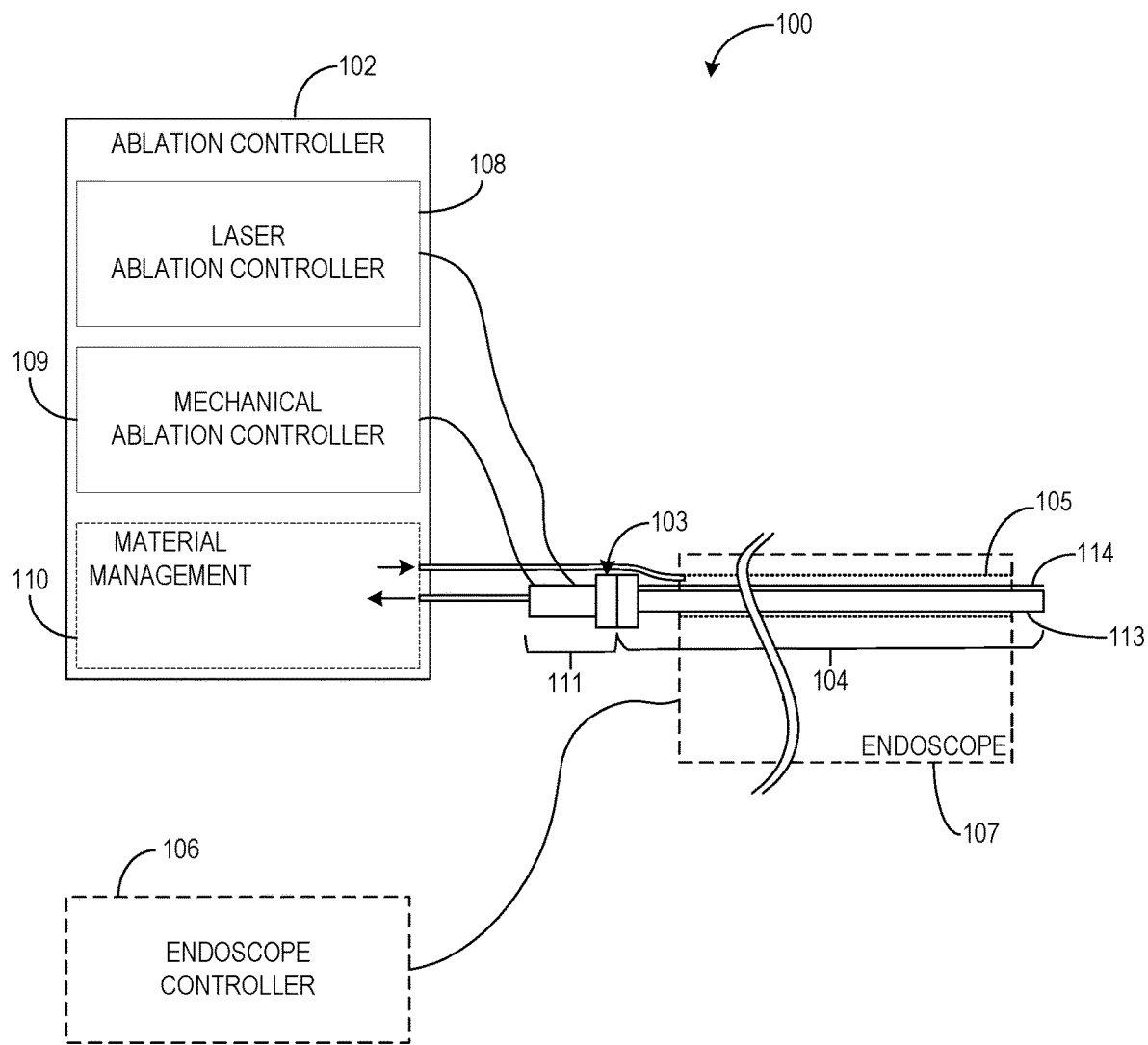
FIG. 1 illustrates generally an example of portions of an ablation system.

FIG. 1 illustrates generally an example of portions of an ablation system 100. The system can include an ablation controller 102, and an ablation instrument 103. In certain examples, a working lumen of an optional surgical instrument, or an access port, can allow for insertion of at least a portion of an ablation probe 104 of the ablation instrument 103 into an internal structure or region of a patient. The working lumen can be a working channel 105 of an optional surgical instrument such as a working channel 105 of an endoscope instrument of an optional endoscopic system. An optional endoscopic system can include an endoscope controller 106 with a light source, and an endoscopic probe, or endoscope 107. The endoscope 107 can include optical fibers or other optical pathway such as can allow light of the light source of the endoscopic system to illuminate a target area from a distal end of the endoscope 107. The endoscope 107 can also use the optical pathway to communicate reflected light (or fluorescence light or other received light) from the target area about the distal end of the endoscope 107, such as to the proximal end of the endoscope 107. The endoscope 107 can include an eyepiece located at or coupled to the proximal end of the endoscope 107, so that a person, such as a surgeon, can observe the conditions at the distal end of the endoscope 107. The endoscopic system can include imaging equipment to receive the light at the proximal end of the endoscope 107. The imaging equipment can include a display, such as to display the image created based on the reflected light. The imaging equipment can include signal processing circuitry, such as to analyze one or more signals based on the reflected light, such as to provide details about certain conditions at the distal end of the endoscope 107. The endoscope 107 can include one or more working channels 105, such as to allow insertion of one or more other surgical instruments to the area at or beyond the distal end of the endoscope 107.

The ablation system 100 can include a laser ablation system, which can include a laser ablation controller 108, a laser source, associated controls, and accessories such as to provide laser ablation energy to the ablation instrument 103. The ablation system 100 can include a mechanical ablation system such as can include a mechanical ablation controller 109, a mechanical energy source, for example, an ultrasonic vibration source, associated controls, and accessories such as to provide the mechanical energy to the ablation instrument 103.

In certain examples, the ablation system may include a material management system 110. The optional material management system 110 can cooperate with the ablation instrument 103 such as to irrigate the distal end of the ablation instrument 103, to aspirate or evacuate material from the distal end of the ablation instrument 103, or to do both. In some examples, the material management system 110 can be part of the endoscope system.

The ablation instrument 103 can include a handle 111, such as can be located at the proximal end of an ablation probe 104. In some examples, a second handle may be located remotely when the ablation procedure is done robotically. The handle 111 can include one or more electrical, mechanical, optical or other interfaces such as for connecting to one or more of the laser ablation controller 108, the mechanical ablation controller 109, or the material management system 110. The handle 111 can include one or more intermediate accessories, such as one or more triggers for actuating the providing of the laser energy and the mechanical energy to the ablation probe 104. The ablation probe 104 can include a tube 113 such as for transmitting the mechanical energy from an electromechanical or other transducer at the handle 111 to a distal end of the tube 113. The ablation probe 104 can also include optical fibers 114 such as for transmitting the laser energy from the handle 111 to the distal end of the tube 113. The optical fibers 114 can be mounted to or integrated with the tube 113. A distal end of the ablation probe 104 can be inserted toward a target site to be used to break up an obstruction or other target near the distal end of the tube 113, such as via mechanical energy, laser energy, or both. An internal channel of the tube 113 can provide a channel such as to allow for irrigation of a target region at or near the distal end of the tube 113, or aspiration or evacuation of broken pieces of the obstruction or other target tissue from the patient's body. In certain examples, the gap formed within the working channel 105 but outside the tube 113 can be used for irrigation of a target region at or near the distal end of the tube 113, or aspiration or evacuation of broken pieces of the obstruction or other target tissue from the patient's body. In some examples, the gap formed within the working channel 105 but outside the tube 113 can be used for a complementary material handling function compared with the internal channel of the tube 113. For example, in certain examples, when the internal channel of the tube 113 is used for aspiration, the gap between the working channel 105 and the outside the tube 113 can be used for irrigation and vice-versa.

Figure 2:
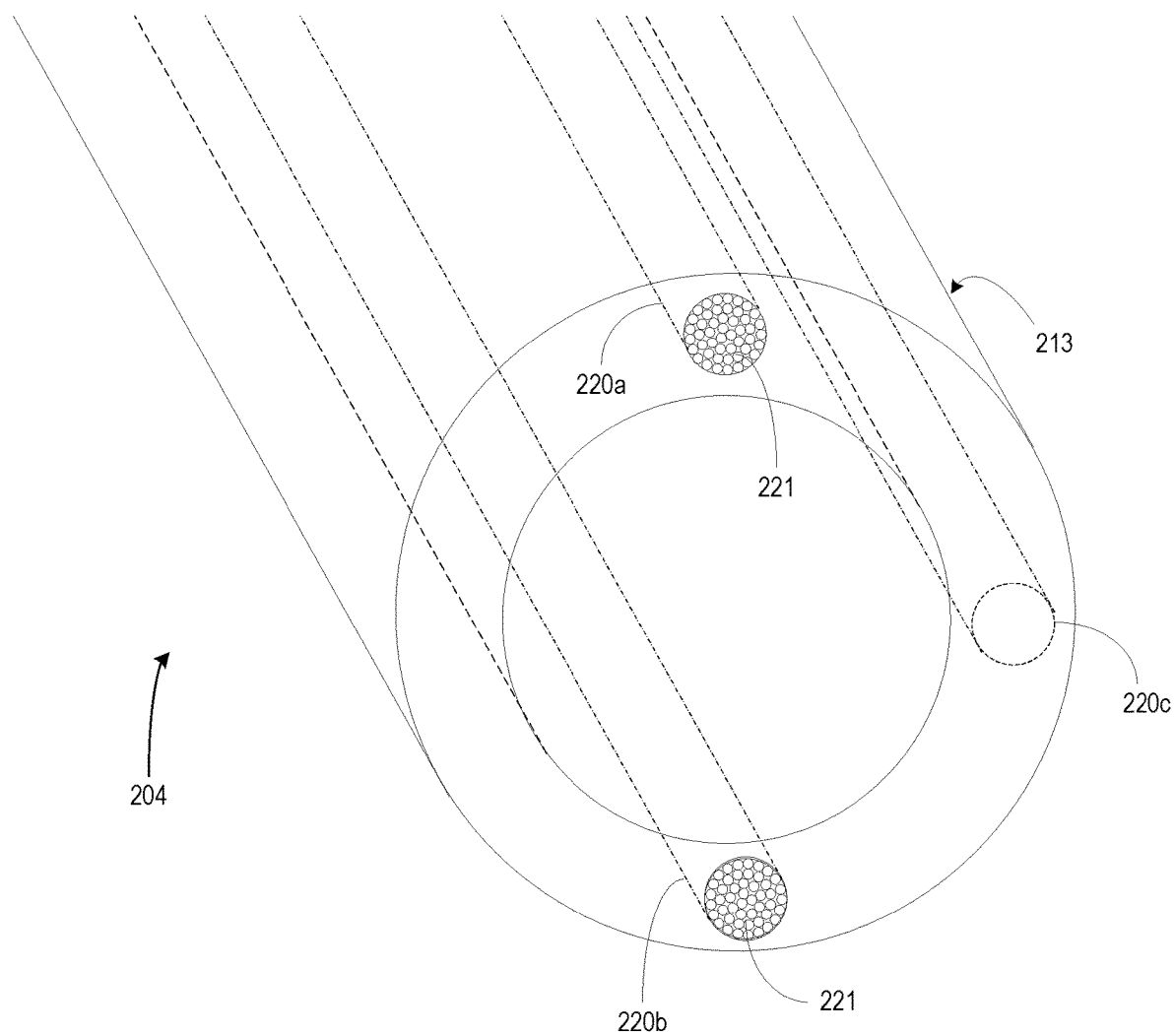
FIG. 2 illustrates generally a distal-end view of an example of portions of a multiple-modality ablation probe.

FIG. 2 illustrates generally a distal-end view of an example of a portion of a multiple-modality ablation probe 204. The multiple-modality ablation probe 204 can include a metal or other rigid tube 213 such as for delivering mechanical ablation energy from an electromechanical or other transducer to an obstruction or other target at or near a distal end of the ablation probe 204. Although flexible tubes or semi rigid tubes may be used to navigate meandering paths to a destination, rigid tubes, though less maneuverable, transmit mechanical ablation energy much more efficiently and with less losses than do semi-rigid or flexible tubes.

Mechanical ablation of an obstruction or other target, such as a kidney stone, can include placing the distal end of the tube 213 against the target stone and mechanically vibrating or oscillating the tube 213. The tube 213 can include one or more holes 220 or passages running longitudinally (lengthwise) along the tube 213, such as within the sidewalls of the tube 213. FIG. 2 illustrates two holes 220a, 220b within the sidewalls of the tube 213, however the tube 213 can include one or more additional optional holes 220. One or more optical fibers 221 can be located such as to extend within a respective one of the sidewall holes 220a, 220b such as can be used to deliver laser energy such as for ablating obstructions or targets. Thus, the multiple-modality probe 204 can ablate an obstruction or target by applying mechanical energy, laser energy, or both.

The handle 111 can include a user interface such as to allow an operator of the system to select or activate mechanical lithotripsy, laser lithotripsy, or both. In an example in which the distal end of the probe 204 includes multiple different optical fiber locations, such as at different locations about a central longitudinal axis of the tube 213, the handle 111 can include a user control to allow the operator to select a particular one or more of such locations at which to deliver laser energy to the target. In such an example, the handle 111 can include one or more beam splitters such as to split and direct an input beam of laser energy to one or more selected optical fibers locations, such as corresponding to different particular sidewall holes 220a, 220b, such as in response to the user selection of a desired particular distal end laser delivery location. In addition to providing a transmission mechanism for delivering mechanical energy to the target, the tube 213 can provide a central or other longitudinal lumen, such as for irrigating or evacuating the area about the distal end of the probe 204. More than one group or bundle of optical fibers 220c can extend longitudinally via the wall of the tube 213, such as at different circumferential or peripheral locations, or offset about the perimeter defined by the tube by at least 5 degrees or more, for example. In certain examples, the tube 213 can be hollow such as to define an internal channel that can be used to irrigate or evacuate or aspirate material about the distal end of the probe 204.

Figure 3:
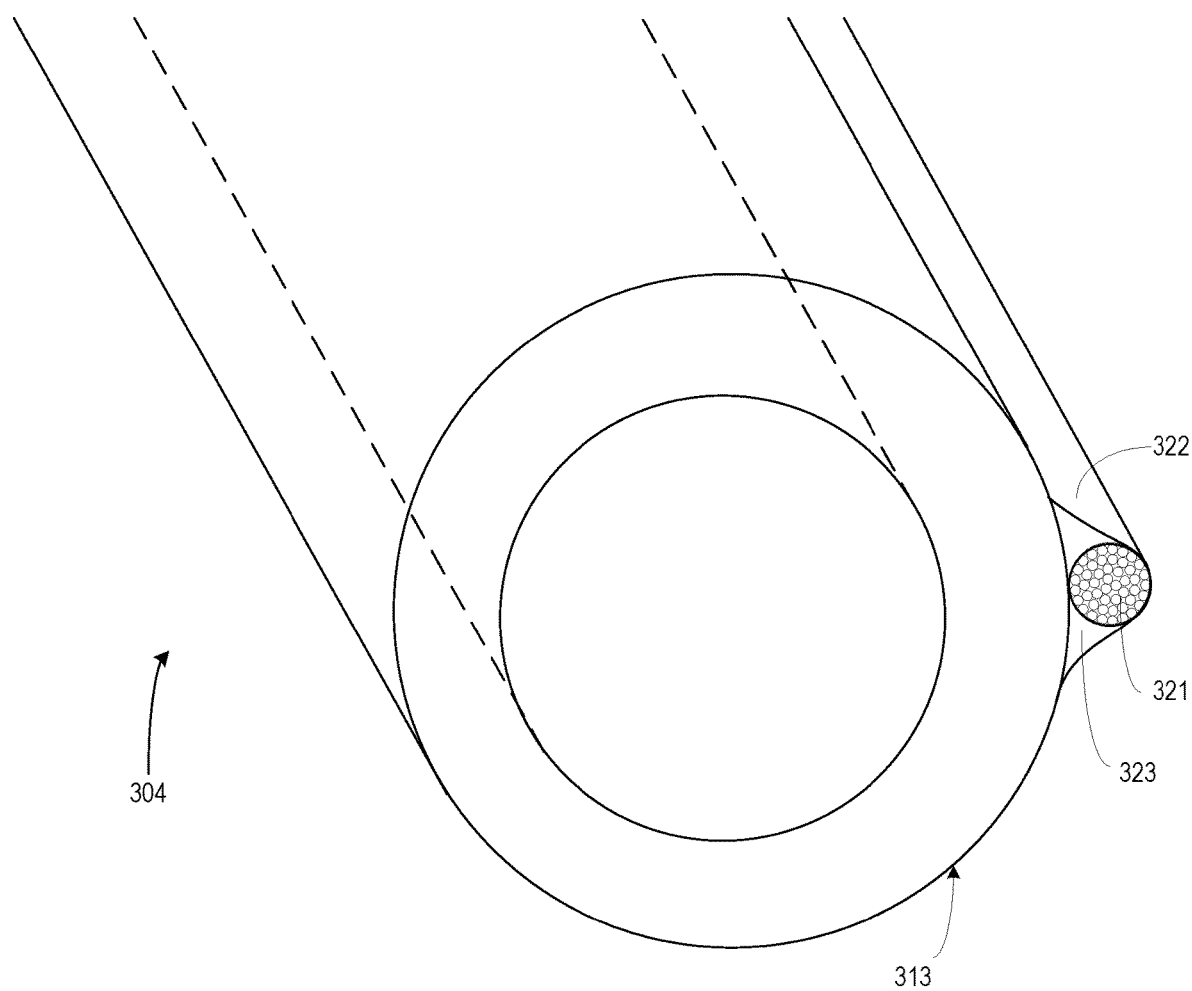
FIG. 3 illustrates generally a distal-end view of an example of portions of a multiple-modality ablation probe.

FIG. 3 illustrates generally a distal-end view of an example of a portion of a multiple-modality ablation probe 304. The multiple-modality ablation probe 304 can include a metal or other rigid tube 313 such as for delivering mechanical ablation energy to an obstruction or other target located at or near the distal end of the ablation probe 304 of FIG. 3. One or more optical fibers 321 can extend within or along the tube 313 such as can be used to apply laser energy to an obstruction. For example, the optical fibers 321 can be held against an exterior surface of the tube 313 by a layer of material, a cover material, or a binding material 322, such as a heat-shrink or other shrink wrap type material, for example. Voids between the cover material and the external surface of the tube 213, such as near the optical fibers 321, can be filled with a surgical-grade silicone or other sealant 322. More than one group or bundle of optical fibers 321 can extend longitudinally along the exterior of the tube 313, such as at different circumferential or peripheral locations, or offset about the tube exterior by at least 5 degrees or more, for example. In certain examples, the tube 313 can be hollow such as to define an internal channel such as can also be used to irrigate or evacuate or aspirate material about the distal end of the probe 304.

As with the example of FIG. 2, the handle 111 of the multiple-modality probe 304 can include various user controls such as for controlling the modulating of the mechanical energy, the laser energy, or both. In addition, where the multiple-modality probe 304 includes multiple bundles of optical fibers 321 extending with the tube 313 toward the distal end, the handle can include one or more beam splitters to allow the user to select which optical fibers transmit the laser energy to the obstruction.

Figure 4:
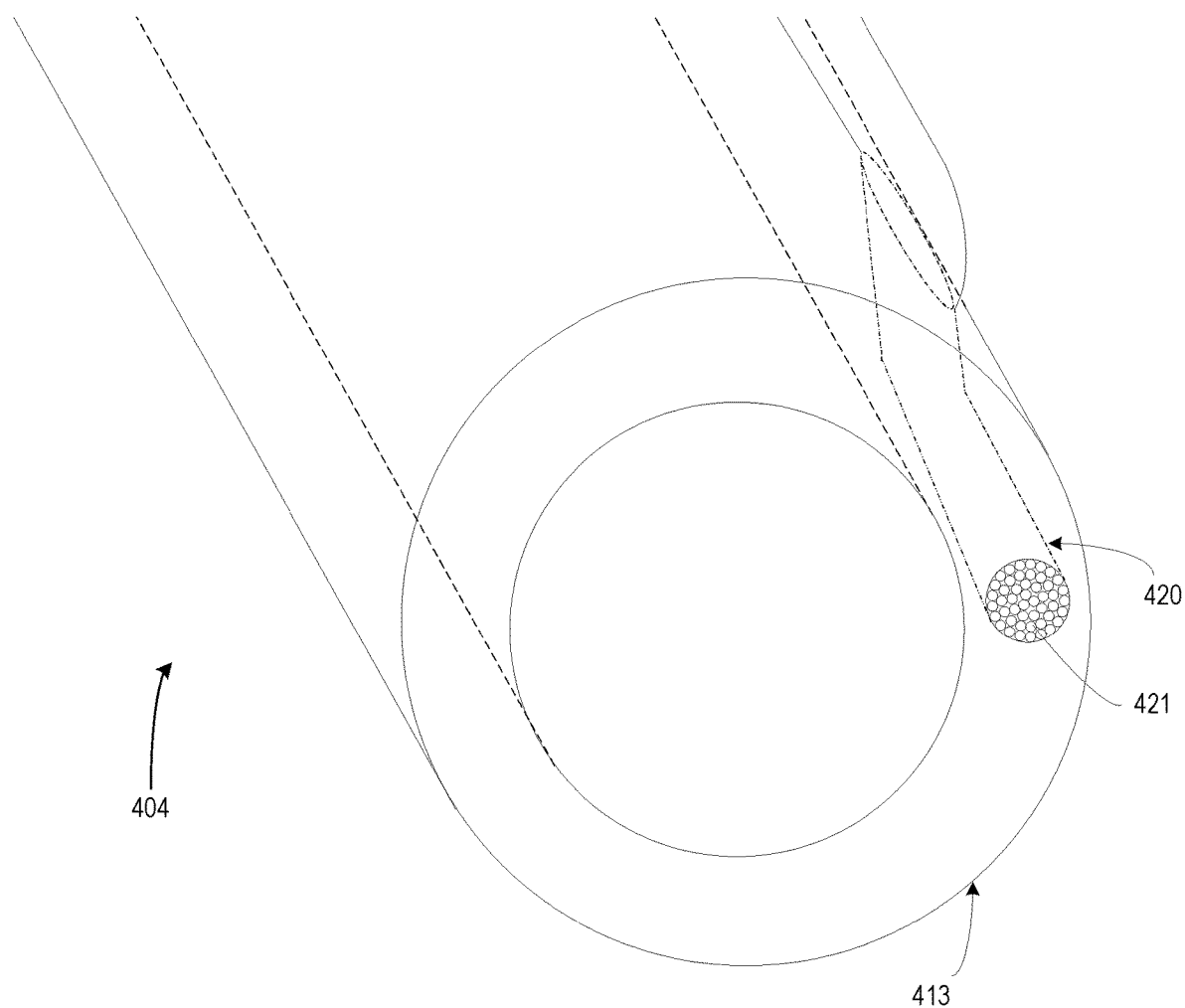
FIG. 4 illustrates generally a distal-end view of an example of portions of a multiple-modality ablation probe.

FIG. 4 illustrates generally a distal-end view of an example of a portion of a multiple-modality ablation probe 404. The multiple-modality ablation probe 404 can include a metal or other rigid tube 413 such as for delivering mechanical ablation energy to an obstruction or other target. One or more optical fibers 421 can extend along the tube 413, such as can be used to apply laser energy to an obstruction or other target located at or near a distal end of the probe 404. The bundle or other arrangement of optical fibers 421 can be held against an exterior surface of the tube 413, such as with a cover or binding material, such as a heat-shrink or other shrink wrap material, for example. Near the distal end of the tube 413, the optical fibers 421 can follow a recess in the exterior of the tube 413 and, via a portal, can transition to a hole 420 within the sidewall of the tube 413, such as can provide a passage for the optical fibers 421 to a termination of the hole 420 at the distal end of the tube 413. Voids between the cover material and the external surface of the tube 413, such as near the optical fibers 421, can be filled with a surgical-grade silicone or other sealant. More than one group or bundle of optical fibers 421 can extend along the exterior of the tube 413 before transitioning via a portal to a corresponding hole providing a passage within the sidewall of the tube 413. Such additional portals can be angularly offset from other portals by 5 degrees or more with respect to a centerline of the tube 404. In certain examples, the tube 413 can be hollow such as to define an internal channel such as can also be used to irrigate or evacuate or aspirate material about the distal end of the probe 404.

As with the examples of FIGS. 2 and 3, the handle 111 of the multiple-modality probe 404 can include various controls such as for modulating the mechanical energy, the laser energy, or both, or for selecting activation of particular ones of multiple bundles of optical fibers 421 extending along the tube 413 toward its distal end. The handle 111 can include one or more beam splitters such as to allow the user to select which optical fibers transmit the laser energy to the obstruction or other target.

Figure 5:
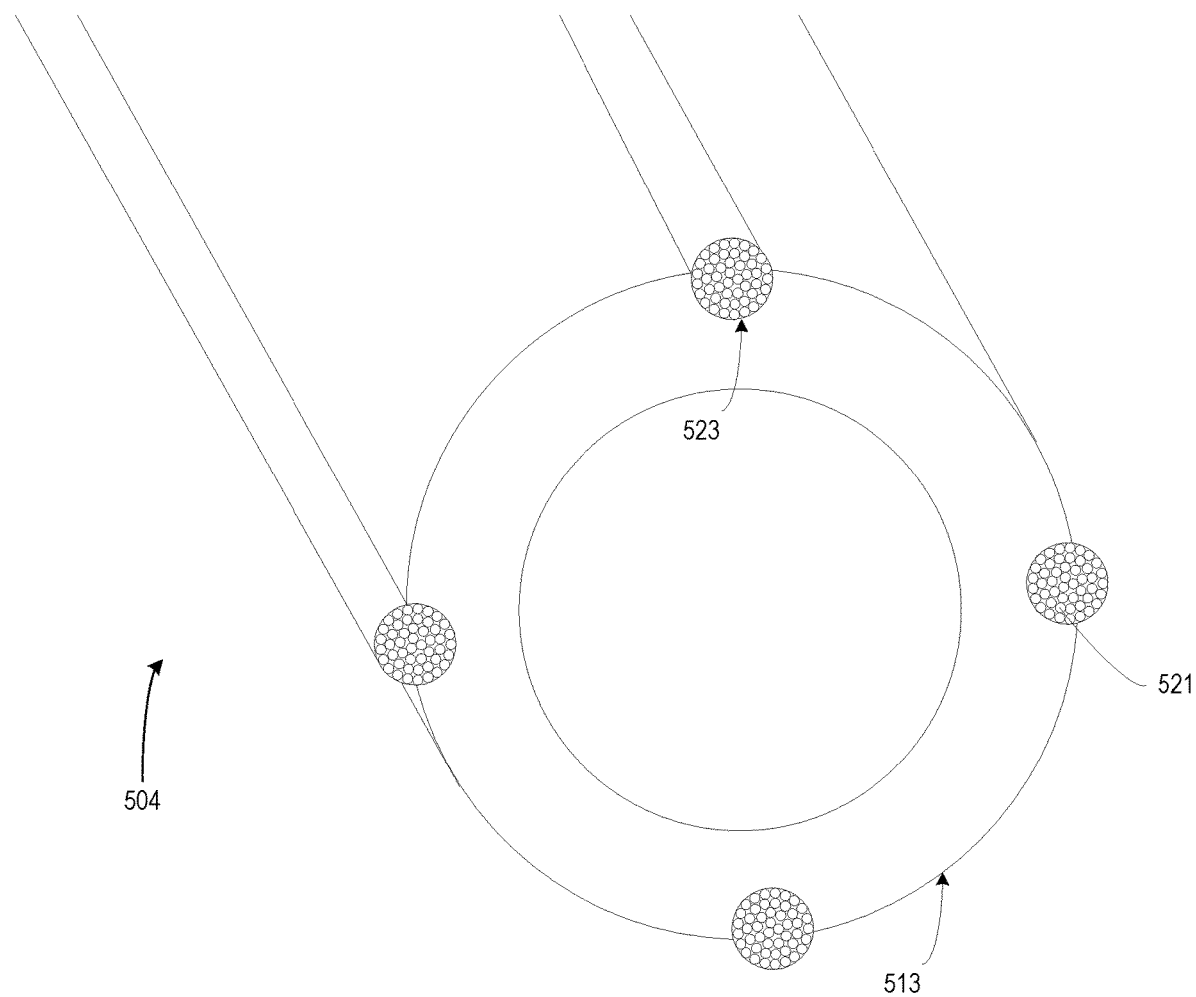
FIG. 5 illustrates generally a distal-end view of an example of portions of a multiple-modality ablation probe.

FIG. 5 illustrates generally a distal-end view of an example of a portion of a multiple-modality ablation probe 504. The multiple-modality ablation probe 504 can include a metal or rigid tube 513 such as for delivering mechanical ablation energy to an obstruction. One or more optical fibers 521 can extend along the tube 513, such as can be used to apply laser energy to an obstruction or other target. The tube 513 can include one or more recessed channels 523 on and along an exterior surface of the tube 513, such as to cradle the one or more optical fibers 521. The optical fibers 521 can be held within the channels of the tube 513 such as by a cover or binding material, such as a heat-shrink or other shrink wrap material. Voids between the cover material and the external surface of the tube 513, such as near the optical fibers 521, can be filled with a surgical-grade silicone or other sealant. The multiple-modality probe 504 can include more or fewer bundles of optical fibers 521 than what is shown in FIG. 5.

As with the examples of FIGS. 2-4, the handle 111 of the multiple-modality probe 504 can include various user controls such as for modulating the mechanical energy, the laser energy, or both. Also, where the multiple-modality probe 504 includes multiple bundles of optical fibers 521 extending along the tube 513 toward its distal end, the handle 111 can include one or more beam splitters such as to allow the user to select which particular bundles of the optical fibers 521 transmit the laser energy to the obstruction or other target. In certain examples, the tube 513 can be hollow such as to define an internal channel such as can also be used to irrigate or evacuate or aspirate material about the distal end of the probe 504.

Figure 6:
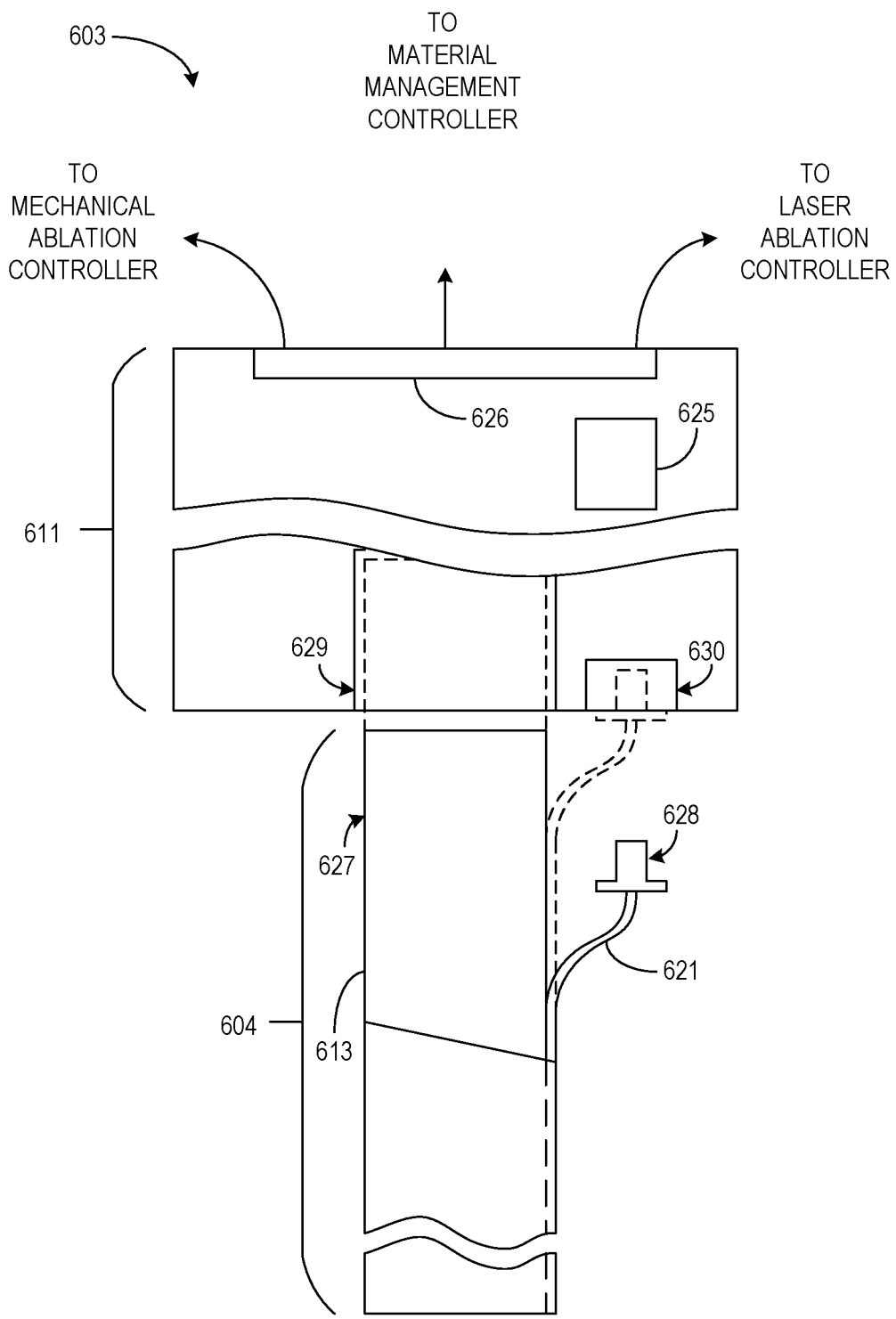
FIG. 6 illustrates generally an example of portions of a multiple-modality, ablation instrument.

FIG. 6 illustrates generally an example of portions of a multiple-modality, ablation instrument 603. The multiple-modality ablation instrument 603 can include a handle 611 and a probe 604. The probe 604 can be user-attachable to or user-detachable from the handle 611, such as can help provide a disposable or one-time use probe 604, such as can be used together with a re-usable handle 611. The handle 611 can provide a user interface such as for positioning and controlling the location of the distal end of the probe 604 when executing an ablation procedure.

The handle 611 can also include a control interface 625 that can allow user control of ablation, such as ablation modality (e.g., mechanical, laser, or both), ablation energy intensity, duty-cycle, actuation, selection of the number and specific bundles of optical fibers to be used to apply laser ablation energy, or other characteristic. The control interface 625 can include, for example, one or more switches, dials, buttons, triggers, or any combination thereof. The handle 611 can include one or more equipment interfaces 626 such as to connect the ablation instrument 603 to a mechanical ablation controller 109, a laser ablation controller 108, a material management system 108, or other control device, signal processing device, or visualization or imaging device, among other things.

The probe 604 can include a tube 613 such as for applying mechanical ablation energy to an obstruction or other target and one or more optical fibers 621 such as for applying laser energy to an obstruction or other target. As discussed above, the tube 613 can be hollow such as to define an internal channel such as can also be used to irrigate or evacuate or aspirate material about the distal end of the probe 604. In some examples, the internal channel of the tube can be used to pass an ancillary instrument. The probe 604 can also include a handle interface 627, 628 such as for connecting to a probe interface 629, 630 of the handle 611. Each of the probe interface 629, 630 and the handle interface 627, 628 can include a portion of a mechanical ablation tube connector 627, 629 and a portion of a laser ablation optical fiber connector 628, 630 to form connector assembly for end-user attachment. The mechanical ablation tube connector 627, 629 can include a connector that can be configured to efficiently transfer to the tube 613 mechanical ablation energy from an electromechanical or other transducer located at the handle 611. In an example, the tube connector 627, 629 can include a snap-fit or threaded connector. The optical fiber connector 628, 630 can include a connector to mate ends of optical fibers, or ends of bundles of optical fibers, such as to efficiently transfer laser ablation energy from optical fibers of the handle 611 to the optical fibers 621 of the probe 604. The ablation instrument 603 can include multiple optical connectors and the handle 611 can include one or more beam splitters, such as to allow optical coupling of a laser energy source with a corresponding bundle of optical fibers of any one, or a combination, of the multiple optical connectors. Having the probe 604 capable of being easily (e.g., threadable, snap-fit, or the like) user-attachable and user-detachable from the handle 611 by the user can allow for the probe 604 to be disposable or one-time use. Disposable or one-time use probes 604 can help reduce cross-patient contamination, lower costs associated with sterilization and tracking, and reduce the possibility of surgical site infection. The straightforward architecture of the probe 604 described herein can help allow for a relatively inexpensive cost of the disposable probe 604. The multiple-modality nature of the ablation provided by the examples of probes such as described herein can help provide the user with additional modality flexibility, such as can be used during an ablation procedure without the burden of removing one probe from the patient, inserting a different new probe into the patient, and then navigating the distal end of the new probe to the same surgical site.

Figure 7:
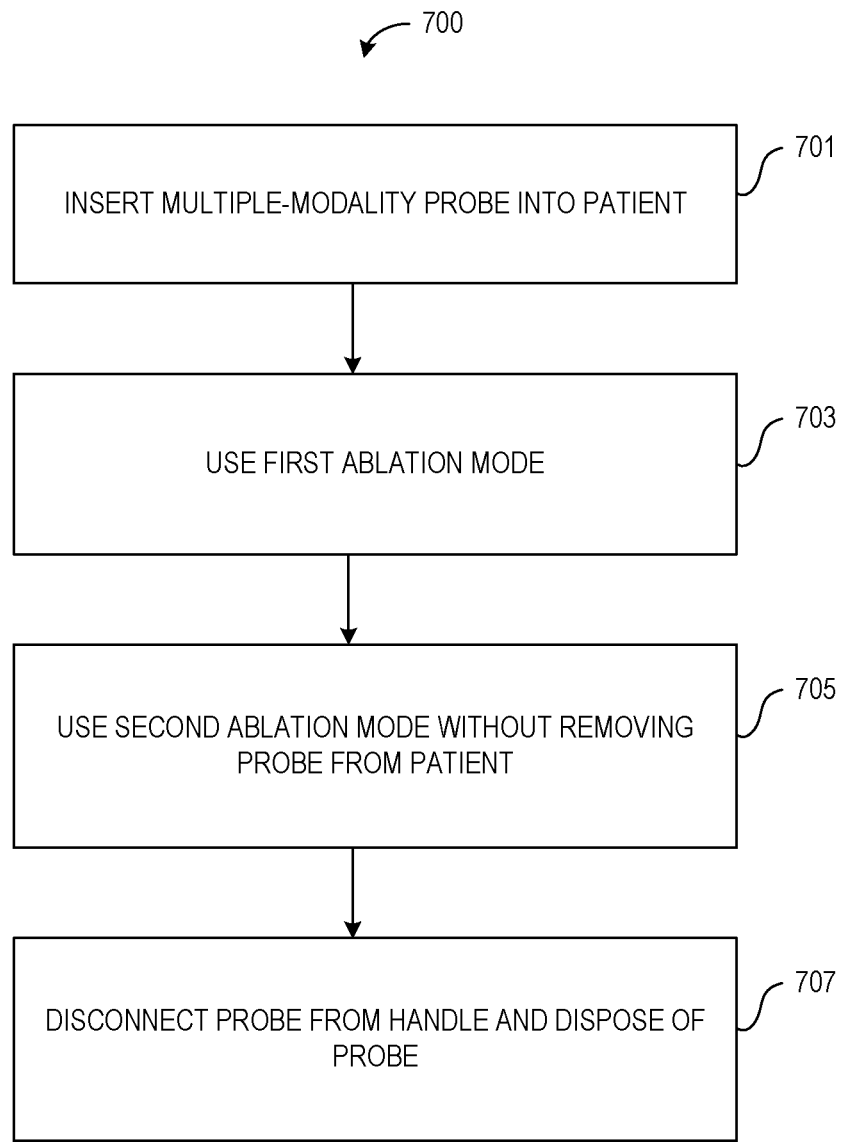
FIG. 7 illustrates generally an example of a method of operating a multiple-modality ablation system.

FIG. 7 illustrates generally an example of a method 700 of operating a multiple-modality ablation system. At 701, a distal portion of a multiple-mode ablation probe can be inserted into a patient. At 703, mechanical ablation energy can be applied to treat a condition of the patient such as to ablate (e.g., via mechanical impact or vibration) a kidney stone, for example. At 705, without requiring an end-user removing the multiple-modality probe from the patient, laser energy can be applied to the patient such as to ablate a smaller stone or a less dense portion of a stone. It may be desirable to first apply the laser energy to a target, then apply the mechanical energy to the same or different target, such as to induce a crack in a targeted kidney stone via the laser before breaking the targeted kidney stone further via mechanical impact. Iterations or variations in sequencing the applying of mechanical and laser energy can be flexibly applied by the surgeon using a single, multi-modality instrument that does not require interchanging an instrument to switch modalities. At 707, the probe can be withdrawn from the patient, disconnected from the handle and disposed of.

Figure 8:
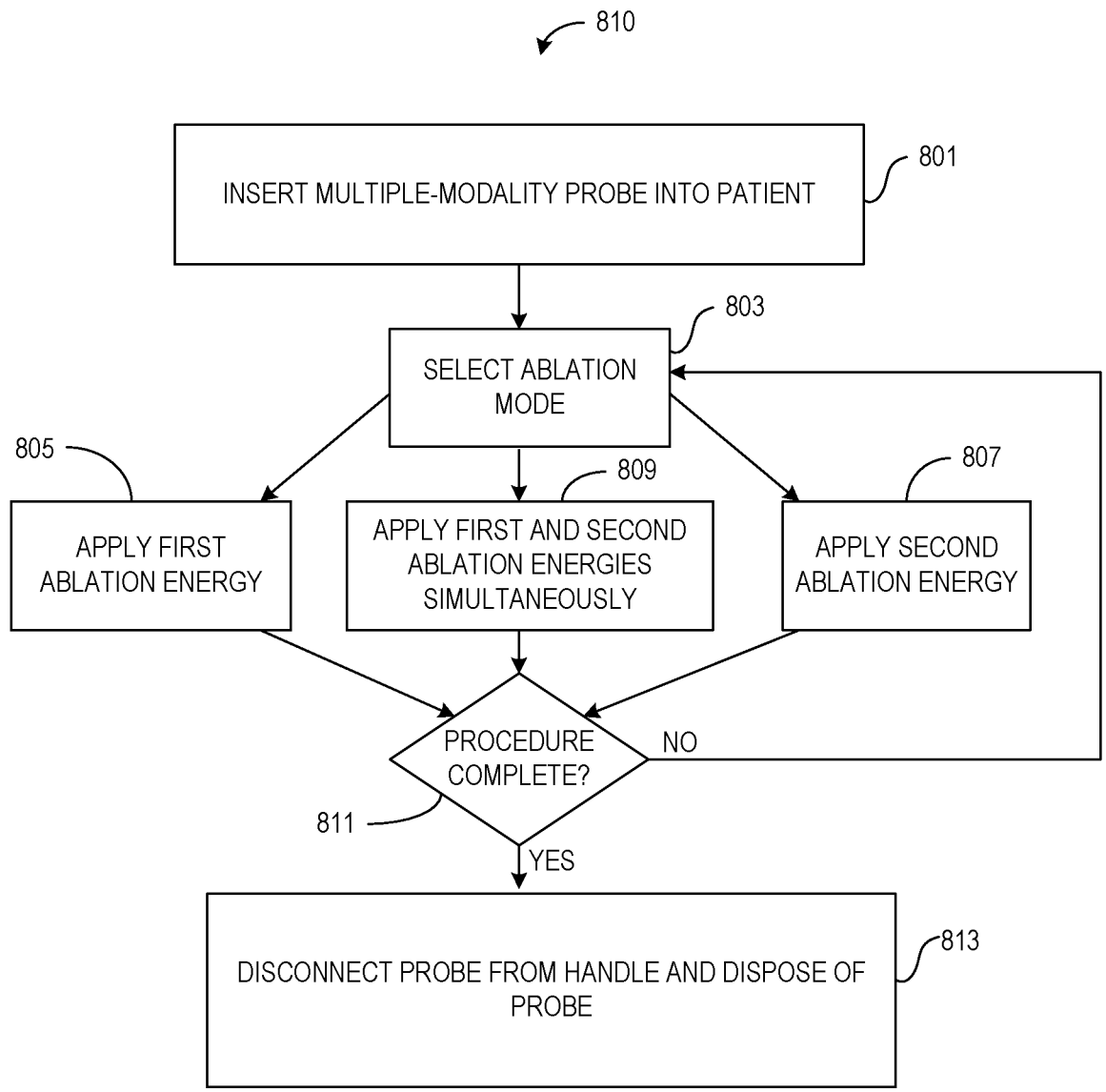
FIG. 8 illustrates generally an example of a method of operating a multiple-modality ablation system.

FIG. 8 illustrates generally an example of a method 800 of operating a multiple-modality ablation system. At 803, a mode of delivering ablation energy can be selected. At 805, a first type of ablation energy, such as mechanical ablation energy, can be applied to a target. At 807, is selected, a second type of ablation energy, such as laser ablation energy, can be applied to a target. At 809, if selected, both the first type of ablation energy and the second type of ablation energy can be applied to a target simultaneously. At 811, if the procedure is not complete, additional ablation energy can be applied. If the procedure is complete, at 813, the probe can be withdrawn from the patient, disconnected from the handle and disposed of.

Thus, the multiple-modality probe can help allow the surgeon to have additional, easy-to-use, ablation technique at the surgeon's disposal and without the inefficiencies associated with removing a probe and inserting a new probe. As explained herein, the probe used for a particular procedure can be detached from the handle and discarded, and another relatively inexpensive probe can be user-attached to the handle for the next procedure.

In a first example, Example 1, a lithotripsy probe can include a tube having a first end and a second end, the tube configured to transmit mechanical ablation energy from the first end to the second end, a first optical transmission media coupled and extending with the tube, the first optical transmission media having a first end and a second end, the first transmission media configured to transmit laser energy from the first end of the first optical transmission media to the second end of the first optical transmission media, and a first portion of a connector assembly configured for end-user attachment and detachment of the tube with a mechanical ablation energy source and for end-user attachment and detachment of the first optical transmission media with a laser energy source, the first portion of the connector assembly mechanically coupled with the first end of the tube and with the first end of the first optical transmission media.

In Example 2, the probe of Example 1 can optionally include a second optical transmission media having a second end configured to transmit the laser energy toward a target, wherein the second end of the second optical transmission media is angularly offset from the second end of the first optical transmission media about a longitudinal central axis of the tube.

In Example 3, the first optical transmission media of any one or more of Examples 1-2 optionally is coupled to and extends along an external surface of the tube.

In Example 4, the first optical transmission media of any one or more of Examples 1-3 optionally is integrated within a portion of a sidewall of the tube and terminates within the sidewall of the tube at the second end of the tube. In Example 5, the first optical transmission media of any one or more of Examples 1~4 optionally is integrated within a sidewall of the tube.

In Example 6, an exterior surface of the tube of any one or more of Examples 1-5 optionally includes a channel extending parallel with a length of the tube.

In Example 7, the first optical transmission media of any one or more of Examples 1-6 optionally is positioned within the channel.

In Example 8, the probe of any one or more of Examples 1-7 optionally includes a layer of material configured to mechanically secure the first optical transmission media to the exterior surface of the tube.

In Example 9, the probe of any one or more of Examples 1-8 optionally includes a sealant configured to occupy a region between the layer of material and the exterior surface of the tube.

In Example 10, the first portion of the connector assembly of any one or more of Examples 1-9 optionally is configured to engage with a handle, the handle including a second portion of the connector assembly.

In Example 11, an ablation system can include a first source configured to generate mechanical ablation energy, a second source configured to generate laser ablation energy, and a probe assembly configured to direct the mechanical ablation energy and the laser ablation energy toward a target. The probe assembly can includes handle and a probe and the probe configured for user-attachment to the handle. The probe can include a tube having a first end and a second end, the tube configured to transmit the mechanical ablation energy from the first end to the target via contact of the target with the second end, a first optical fiber mechanically coupled and extending with the tube, the first optical fiber having a first end and a second end, the first optical fiber configured to transmit the laser ablation energy from the first end of the first optical fiber to the target via the second end of the first optical fiber, and a first portion of a connector assembly configured user-attachment of the tube and the first optical fiber with the first source and with the second source, respectively, the first portion mechanically coupled with the first end of the tube and with the first end of the first optical fiber.

In Example 12, the tube and the first optical fiber of any one or more of Examples 1-11 optionally are configured to extend together through a lumen of an endoscope.

In Example 13, the probe of any one or more of Examples 1-12 optionally includes a second optical fiber having a second end configured to transmit the laser energy to the target, wherein the second end of the second optical fiber is angularly offset from the second end of the first optical fiber about a longitudinal central axis of the tube at the second end of the tube.

In Example 14, the system of any one or more of Examples 1-13 optionally includes a beam splitter configured to selectively direct the laser ablation energy to one or more optical fibers of a plurality of optical fibers, the plurality of optical fibers including the first optical fiber and the second optical fiber.

In Example 15, a method can include inserting a portion of a multiple-modality ablation probe into a patient, delivering mechanical ablation energy from a distal end of a tube of the multiple-modality ablation probe, and transmitting laser ablation energy from a distal end of a first optical pathway of the multiple-modality ablation probe.

In Example 16, the method of any one or more of Examples 1-15 optionally does not require removing the probe from the patient to switch between delivering the time-varying mechanical ablation energy and the laser ablation energy. In Example 17, the delivering mechanical ablation energy and the transmitting laser ablation energy of any one or more of Examples 1-16 optionally includes delivering mechanical ablation energy from a distal end of a tube of the multiple-modality ablation probe simultaneously with transmitting laser ablation energy from a distal end of a first optical pathway of the multiple-modality ablation probe.

In Example 18, the method of any one or more of Examples 1-17 optionally includes irrigating an area about a distal end of the tube using a channel of the tube.

In Example 19, the method of any one or more of Examples 1-18 optionally includes evacuating material from about a distal end of the tube using a channel of the tube.

In Example 20, the method of any one or more of Examples 1-19 optionally includes transmitting the laser ablation energy from a distal end of a second optical pathway of the multiple-modality ablation probe, the second optical pathway angularly offset from the first optical pathway by at least 5 degrees about a centerline of the tube.

In Example 21, the method of any one or more of Examples 1-20 optionally includes adjusting a beam splitter to switch transmitting of the laser energy via the first optical pathway to transmitting of the laser energy via the second optical pathway.

In Example 22, the delivering mechanical ablation energy of any one or more of Examples 1-21 optionally includes delivering ultrasonic ablation energy from a distal end of a tube of the multiple-modality ablation probe.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, the terms "including" and "comprising" are open-ended, that is, a system, device, article, composition, formulation, or process that includes elements in addition to those listed after such a term are still deemed to fall within the scope of subject matter discussed. Moreover, such as may appear in a claim, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of a claim. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment.

The following aspects are hereby incorporated into the Detailed Description as examples or embodiments, with each aspect standing on its own as a separate embodiment, and it is contemplated that such embodiments can be combined with each other in various combinations or permutations.

What is claimed is:

1. A lithotripsy probe comprising:
   a tube having a first end and a second end, the tube configured to transmit mechanical ablation energy from the first end to the second end;
   a first optical transmission media coupled and extending with the tube, the first optical transmission media having a first end and a second end, the first optical transmission media configured to transmit laser energy from the first end of the first optical transmission media to the second end of the first optical transmission media;
   a removable handle including a first interface configured for connection to an external laser energy source and a second interface configured for connection to an external mechanical ablation energy source; and
   the tube including a first portion of a connector assembly configured for end-user attachment and detachment of the tube with the mechanical ablation energy source and for end-user attachment and detachment of the first optical transmission media with the laser energy source, the first portion of the connector assembly mechanically coupled with the first end of the tube and with the first end of the first optical transmission media; the handle including a second portion of the connector assembly, the second portion of the connector assembly configured to engage with the first portion of the connector assembly to operably couple the tube and the first optical transmission media to the external mechanical ablation energy source and the external laser energy source, respectively.

2. The probe of claim 1, including a second optical transmission media having a second end configured to transmit the laser energy toward a target, wherein the second end of the second optical transmission media is angularly offset from the second end of the first optical transmission media about a longitudinal central axis of the tube.

3. The probe of claim 1, wherein the first optical transmission media is coupled to and extends along an external surface of the tube.

4. The probe of claim 3, wherein the first optical transmission media is integrated within a portion of a sidewall of the tube and terminates within the sidewall of the tube at the second end of the tube.

5. The probe of claim 1, wherein the first optical transmission media is integrated within a sidewall of the tube.

6. The probe of claim 1, wherein an exterior surface of the tube includes a channel extending parallel with a length of the tube.

7. The probe of claim 6, wherein the first optical transmission media is positioned within the channel.

8. The probe of claim 7, including a layer of material configured to mechanically secure the first optical transmission media to the exterior surface of the tube.

9. The probe of claim 8, including a sealant configured to occupy a region between the layer of material and the exterior surface of the tube.

10. An ablation system including:
a first source configured to generate mechanical ablation energy;
a second source configured to generate laser ablation energy; and
a probe assembly configured to direct the mechanical ablation energy and the laser ablation energy toward a target;
wherein the probe assembly includes a removable handle and a probe, the probe configured for user-attachment to the handle, the probe comprising:
a tube having a first end and a second end, the tube configured to transmit the mechanical ablation energy from the first end to the target via contact of the target with the second end;
a first optical fiber mechanically coupled and extending with the tube, the first optical fiber having a first end and a second end, the first optical fiber configured to transmit the laser ablation energy from the first end of the first optical fiber to the target via the second end of the first optical fiber; and
a first portion of a connector assembly configured for user-attachment of the tube to the handle; and
wherein the handle comprises a second portion of the connector assembly, the second portion of the connector assembly configured to engage with the first portion of the connector assembly to operably couple the tube and the first optical fiber to the first source configured to generate mechanical ablation energy and the second source configured to generate laser ablation energy, respectively.

11. The system of claim 10, wherein the tube and the first optical fiber are configured to extend together through a lumen of an endoscope.

12. The system of claim 10, wherein the probe includes a second optical fiber having a second end configured to transmit the laser energy to the target, wherein the second end of the second optical fiber is angularly offset from the second end of the first optical fiber about a longitudinal central axis of the tube at the second end of the tube.

13. The system of claim 12, including a beam splitter configured to selectively direct the laser ablation energy to one or more optical fibers of a plurality of optical fibers, the plurality of optical fibers including the first optical fiber and the second optical fiber.

14. A method comprising:
inserting a portion of a multiple-modality ablation probe into a patient, the probe including a tube defining a first portion of a connector assembly, a first optical transmission media extending with the tube, and a removable handle defining a second portion of the connector assembly, wherein the second portion of the connector assembly engages with the first portion of the connector assembly to operably couple the tube and the first optical transmission media to an external mechanical ablation energy source and an external laser energy source, respectively;
delivering mechanical ablation energy from a distal end of the tube of the multiple-modality ablation probe; and
transmitting laser ablation energy from a distal end of the first optical transmission media of the multiple-modality ablation probe.

15. The method of claim 14, wherein the method does not require removing the probe from the patient to switch between delivering the time-varying-mechanical ablation energy and the laser ablation energy.

16. The method of claim 14, wherein the delivering mechanical ablation energy and the transmitting laser ablation energy includes delivering mechanical ablation energy from the distal end of the tube of the multiple-modality ablation probe simultaneously with transmitting laser ablation energy from the distal end of the first optical pathway transmission media of the multiple-modality ablation probe.

17. The method of claim 14, including irrigating an area about the distal end of the tube using a channel of the tube.

18. The method of claim 14, including evacuating material from about the distal end of the tube using a channel of the tube.

19. The method of claim 14, including transmitting the laser ablation energy from a distal end of a second optical transmission media of the multiple-modality ablation probe, the second optical transmission media angularly offset from the first optical transmission media by at least 5 degrees about a centerline of the tube.

20. The method of claim 14, wherein the method includes adjusting a beam splitter to switch transmitting of the laser energy via the first optical transmission media to transmitting of the laser energy via a second optical transmission media.

21. The method of claim 14, wherein the delivering mechanical ablation energy includes delivering ultrasonic ablation energy from the distal end of the tube of the multiple-modality ablation probe.

* * * * *

UNITED STATES PATENT AND TRADEMARK OFFICE
CERTIFICATE OF CORRECTION

PATENT NO. : 12,161,407 B2
APPLICATION NO. : 17/184701
DATED : December 10, 2024
INVENTOR(S) : Pyro et al.

Page 1 of 1

It is certified that error appears in the above-identified patent and that said Letters Patent is hereby corrected as shown below:

In the Claims

In Column 12, Line 36, in Claim 15, delete "time-varying-mechanical" and insert --mechanical-- therefor In Column 12, Line 43, in Claim 16, after "optical", delete "pathway"

Signed and Sealed this
Twenty-sixth Day of August, 2025

Coke Morgan Stewart
*Acting Director of the United States Patent and Trademark Office*